United States Patent
Thenuwara et al.

(10) Patent No.: US 9,033,869 B2
(45) Date of Patent: *May 19, 2015

(54) COCHLEAR LEAD

(75) Inventors: Chuladatta Thenuwara, Castiac, CA (US); Mark Downing, Valencia, CA (US)

(73) Assignee: ADVANCED BIONICS, LLC, Valencia, CA (US)

(*) Notice: Subject to any disclaimer, the term of this patent is extended or adjusted under 35 U.S.C. 154(b) by 2 days.

This patent is subject to a terminal disclaimer.

(21) Appl. No.: 13/463,450

(22) Filed: May 3, 2012

(65) Prior Publication Data
US 2012/0221088 A1    Aug. 30, 2012

Related U.S. Application Data

(63) Continuation-in-part of application No. 12/789,264, filed on May 27, 2010.

(51) Int. Cl.
*A61N 1/05* (2006.01)
*A61N 1/36* (2006.01)

(52) U.S. Cl.
CPC .......... *A61N 1/0541* (2013.01); *A61N 1/36032* (2013.01)

(58) Field of Classification Search
CPC .................. A61N 1/0541; A61N 1/36032
USPC .......................... 607/116, 136, 137
See application file for complete search history.

(56) References Cited

U.S. PATENT DOCUMENTS

| | | | |
|---|---|---|---|
| 5,437,632 A | 8/1995 | Engelson |
| 5,470,322 A | 11/1995 | Horzewski et al. |
| 5,476,497 A | 12/1995 | Mower et al. |
| 5,573,520 A | 11/1996 | Schwartz et al. |
| 5,630,839 A | 5/1997 | Corbett et al. |
| 5,653,742 A | 8/1997 | Parker et al. |
| 5,762,630 A | 6/1998 | Bley et al. |
| 5,800,500 A | 9/1998 | Spelman et al. |
| 5,999,859 A | 12/1999 | Jolly |

(Continued)

FOREIGN PATENT DOCUMENTS

| | | |
|---|---|---|
| EP | 1341578 B1 | 4/2002 |
| EP | 2209520 A1 | 7/2003 |

(Continued)

OTHER PUBLICATIONS

Rebscher et al, Strategies to Improve Electrode Positioning and Safety in Cochlear Implants, IEEE Trans Biomed Eng, 46(3) 340-352, 1999.

(Continued)

*Primary Examiner* — Joseph Dietrich
(74) *Attorney, Agent, or Firm* — Steven L. Nichols; Van Cott, Bagley, Cornwall & McCarthy P.C.

(57) ABSTRACT

A cochlear lead includes a plurality of electrodes configured to stimulate an auditory nerve from within a cochlea and a flexible body supporting the plurality of electrodes along a length of the flexible body. A stiffening element is slidably encapsulated within the flexible body, the stiffening element extending past a most distal electrode at the tip of the cochlear lead, wherein a distal portion of the stiffening element plastically deforms upon insertion into a curved portion of the cochlea.

18 Claims, 9 Drawing Sheets

(56) References Cited

U.S. PATENT DOCUMENTS

| | | | |
|---|---|---|---|
| 6,048,338 A | 4/2000 | Larson et al. | |
| 6,119,044 A | 9/2000 | Kuzma et al. | |
| 6,125,302 A | 9/2000 | Kuzma | |
| 6,321,125 B1 | 11/2001 | Kuzma | |
| 6,368,316 B1 | 4/2002 | Jansen et al. | |
| 6,421,569 B1 | 7/2002 | Treaba et al. | |
| 6,428,489 B1 | 8/2002 | Jacobsen et al. | |
| 6,475,209 B1 | 11/2002 | Larson et al. | |
| 6,556,873 B1 | 4/2003 | Smits | |
| 6,562,021 B1 | 5/2003 | Derbin et al. | |
| 6,604,283 B1 | 8/2003 | Kuzma | |
| 6,757,970 B1 | 7/2004 | Kuzma et al. | |
| 6,858,680 B2 | 2/2005 | Gunatillake et al. | |
| 6,887,235 B2 | 5/2005 | O'Connor et al. | |
| 6,968,238 B1 | 11/2005 | Kuzma | |
| 6,999,821 B2 | 2/2006 | Jenney et al. | |
| 7,047,081 B2 | 5/2006 | Kuzma | |
| 7,050,858 B1 | 5/2006 | Kuzma et al. | |
| 7,063,708 B2 | 6/2006 | Gibson et al. | |
| 7,066,931 B2 | 6/2006 | O'Connor et al. | |
| 7,115,183 B2 | 10/2006 | Larson et al. | |
| 7,146,227 B2 | 12/2006 | Dadd et al. | |
| 7,239,923 B1 | 7/2007 | Tockman et al. | |
| 7,269,461 B2 | 9/2007 | Dadd et al. | |
| 7,272,449 B2 | 9/2007 | Dadd et al. | |
| 7,315,763 B2 | 1/2008 | Kuzma et al. | |
| 7,319,906 B2 | 1/2008 | Kuzma et al. | |
| 7,328,072 B2 | 2/2008 | Milojevic et al. | |
| 7,389,148 B1 | 6/2008 | Morgan | |
| 7,403,823 B1 | 7/2008 | Kroll et al. | |
| 7,451,000 B2 | 11/2008 | Gibson et al. | |
| 7,540,865 B2 | 6/2009 | Griffin et al. | |
| 7,571,012 B2 | 8/2009 | Gibson | |
| 7,742,827 B2 | 6/2010 | Lenarz et al. | |
| 2002/0029074 A1 | 3/2002 | Treaba et al. | |
| 2002/0161114 A1 | 10/2002 | Gunatillake et al. | |
| 2003/0040684 A1 | 2/2003 | Soukup | |
| 2003/0045921 A1 | 3/2003 | Dadd et al. | |
| 2003/0093139 A1 | 5/2003 | Gibson et al. | |
| 2003/0181967 A1 | 9/2003 | Dadd et al. | |
| 2004/0030376 A1 | 2/2004 | Gibson et al. | |
| 2004/0078057 A1 | 4/2004 | Gibson | |
| 2004/0127968 A1 | 7/2004 | Kuzma et al. | |
| 2005/0234535 A1 | 10/2005 | Risi et al. | |
| 2006/0089569 A1 | 4/2006 | Soukup et al. | |
| 2006/0235500 A1 | 10/2006 | Gibson et al. | |
| 2006/0247749 A1 | 11/2006 | Colvin | |
| 2007/0073130 A1 | 3/2007 | Finch et al. | |
| 2007/0073371 A1 | 3/2007 | Dadd et al. | |
| 2007/0127745 A1 | 6/2007 | Gibson | |
| 2007/0162098 A1 | 7/2007 | Risi et al. | |
| 2008/0027527 A1 | 1/2008 | Kuzma et al. | |
| 2008/0077049 A1 | 3/2008 | Hirshman | |
| 2008/0109011 A1 | 5/2008 | Thenuwara et al. | |
| 2008/0269864 A1 | 10/2008 | Dadd et al. | |
| 2009/0030483 A1 | 1/2009 | Risi et al. | |
| 2009/0043358 A1 | 2/2009 | Dadd et al. | |
| 2009/0043369 A1 | 2/2009 | Radeloff | |
| 2009/0043370 A1 | 2/2009 | Gibson et al. | |
| 2009/0165921 A1 | 7/2009 | Kaiser | |
| 2009/0312769 A1 | 12/2009 | Dadd et al. | |
| 2010/0057180 A1 | 3/2010 | Gibson et al. | |
| 2010/0106232 A1 | 4/2010 | Dadd et al. | |
| 2010/0204768 A1 | 8/2010 | Jolly et al. | |
| 2010/0287770 A1 | 11/2010 | Dadd et al. | |
| 2011/0016710 A1 | 1/2011 | Dadd | |
| 2011/0319907 A1 | 12/2011 | Gallegos et al. | |
| 2012/0035615 A1 | 2/2012 | Koester et al. | |

FOREIGN PATENT DOCUMENTS

| | | |
|---|---|---|
| EP | 1604626 A2 | 12/2005 |
| EP | 1604626 A3 | 12/2005 |
| EP | 1189560 B1 | 3/2006 |
| EP | 1604626 B1 | 12/2008 |
| EP | 2042137 A1 | 4/2009 |
| WO | 9306698 | 4/1993 |
| WO | 9710784 | 3/1997 |
| WO | 0071063 | 11/2000 |
| WO | 0228473 | 4/2002 |
| WO | 0228474 | 4/2002 |
| WO | 0230507 | 4/2002 |
| WO | 0232498 | 4/2002 |
| WO | 0243623 | 6/2002 |
| WO | 02094334 | 11/2002 |
| WO | 03049658 | 6/2003 |
| WO | 2004002570 | 1/2004 |
| WO | 2007002879 A1 | 3/2007 |
| WO | 2007027879 | 3/2007 |
| WO | 2009065127 A1 | 5/2009 |
| WO | 2009065171 A1 | 5/2009 |
| WO | 2009079704 A1 | 7/2009 |
| WO | 2010015016 A1 | 2/2010 |
| WO | 2010015017 A1 | 2/2010 |
| WO | 2010091237 A2 | 8/2010 |
| WO | 2010091237 A3 | 11/2010 |
| WO | 2011149695 A1 | 12/2011 |

OTHER PUBLICATIONS

Kha et al, Stiffness Properties of Nucleus Standard Straight and Contour Electrode Arrays, Med and Eng Phys 26 677-685, 2004.

He, Bo et al., Surface Texture effect on Friction of a Microtextured Polydimethylsiloxane, Tribology Letters, vol. 31, No. 3, Aug. 12, 2008; pp. 1-11.

Stover, Timo et al., "Microstructured Cochlear Implant Electrodes," Subproject T1 of Collaborative Research Center 599; pp. 1-2; Feb. 7, 2011.

Lenarz, Thomas et al., "Nerve-Electrode Interface," Subproject D2 of Collaborative Research Center 599; pp. 1-2; Feb. 7, 2011.

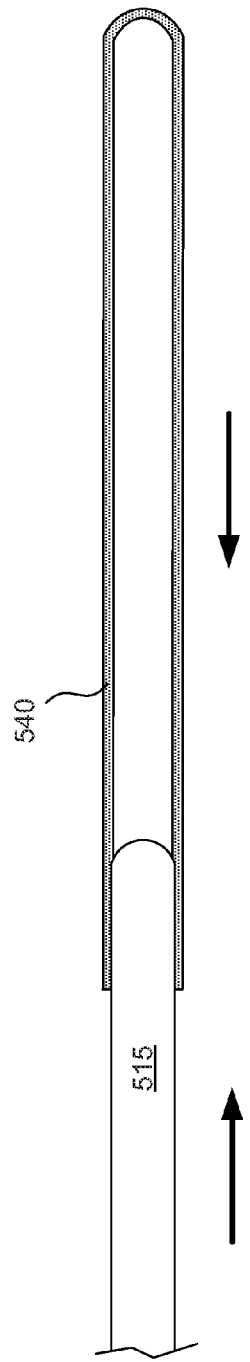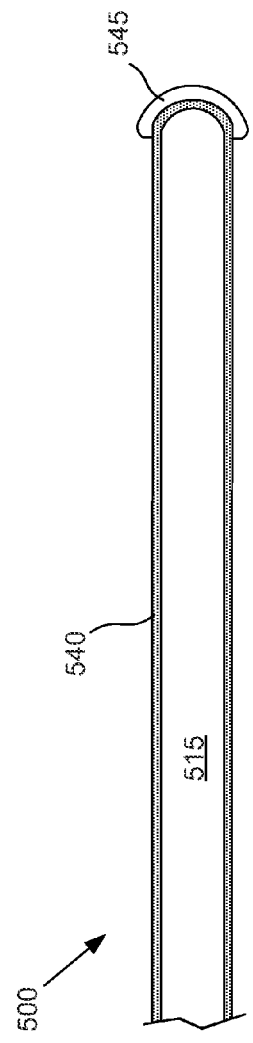

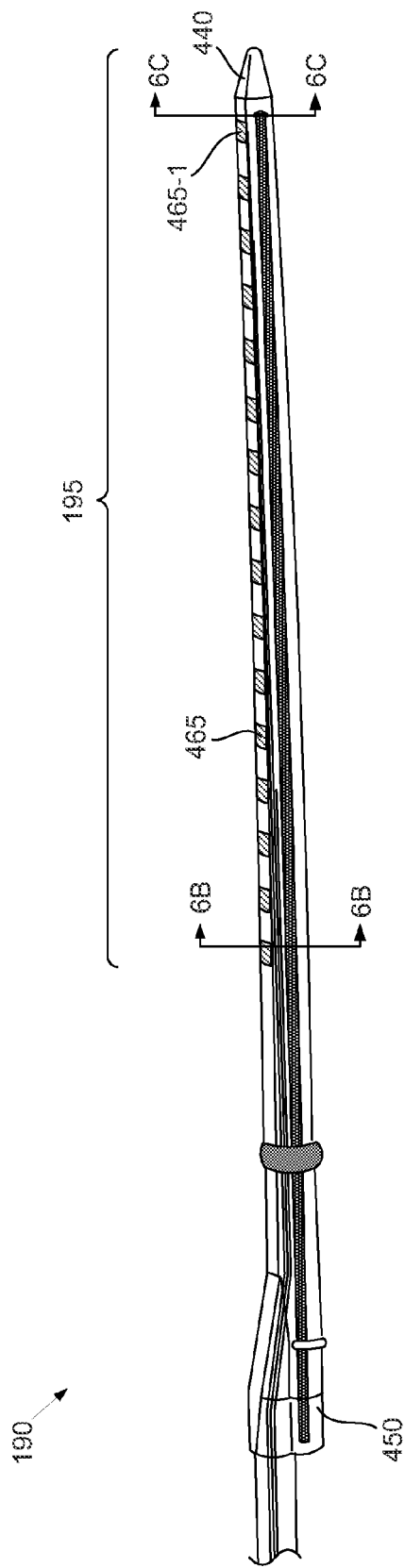
Fig. 6A
Fig. 6B
Fig. 6C

900

```
┌─────────────────────────────────────┐
│ Removing a previous cochlear lead   │
│ from a cochlea.                     │
│              905                    │
└─────────────────────────────────────┘
                 │
                 ▼
┌─────────────────────────────────────┐
│ Obtaining a replacement cochlear    │
│ lead having a smaller diameter than │
│ the previous cochlear lead, the     │
│ replacement cochlear lead comprising│
│ a slidably encapsulated stiffener   │
│ extending from an offset gripping   │
│ feature through a cochlear electrode│
│ array past a most distal electrode, │
│ the encapsulated stiffener          │
│ comprising an annealed distal       │
│ portion.                            │
│              910                    │
└─────────────────────────────────────┘
                 │
                 ▼
┌─────────────────────────────────────┐
│ Gripping a proximal end of the      │
│ stiffening element by engaging the  │
│ gripping feature.                   │
│              915                    │
└─────────────────────────────────────┘
                 │
                 ▼
┌─────────────────────────────────────┐
│ Inserting the replacement cochlear  │
│ lead into the cochlea by            │
│ manipulating the proximal end of the│
│ stiffening element to guide the     │
│ cochlear lead into the cavity       │
│ vacated by the previous cochlear    │
│ lead in which the replacement       │
│ cochlear lead is inserted to a      │
│ predetermined depth in the cochlea. │
│              920                    │
└─────────────────────────────────────┘
```

*Fig. 9*

COCHLEAR LEAD

RELATED DOCUMENTS

The present application is a continuation-in-part, and claims the benefit under 35 U.S.C. §120, of U.S. application Ser. No. 12/789,264, filed May 27, 2010, entitled "Cochlear Lead" to Chuladatta Thenuwara et al. This application is incorporated herein by reference in its entirety.

BACKGROUND

Hearing loss can be corrected using a number of approaches, including surgically placing a cochlear implant which includes an electrode array that is inserted into the cochlea of a patient. The electrode array presents electrical stimulation directly to auditory nerve fibers in the cochlea. This leads to the perception of sound in the brain and provides at least partial restoration of hearing function. Occasionally, the cochlear implant may need to be replaced with a new cochlear implant. The original electrode array is removed from the cochlea and a new cochlear lead is inserted. In some instances, the cochlea may have tissue that at least partially occludes the passageway into which the new cochlear lead is to be inserted. This presents a number of challenges that can be addressed by a new cochlear lead design.

BRIEF DESCRIPTION OF THE DRAWINGS

The accompanying drawings illustrate various embodiments of the principles described herein and are a part of the specification. The illustrated embodiments are merely examples and do not limit the scope of the claims.

FIG. 5A is a partial side view of an illustrative stiffening element and sheath, according to one example of principles described herein.

FIG. 5B shows a cross-section of an illustrative stiffening element with a sheath in place and a cap placed over the distal end of the stiffening element, according to one example of principles described herein.

FIG. 6A is a side view of an illustrative cochlear lead, according to one example of principles described herein.

FIGS. 6B-6C are cross-sectional views of the cochlear lead shown in FIG. 6A, according to one example of principles described herein.

FIG. 9 is a flowchart showing an illustrative method for using a cochlear lead, according to one example of principles described herein.

Throughout the drawings, identical reference numbers designate similar, but not necessarily identical, elements.

DETAILED DESCRIPTION

Figure 1:
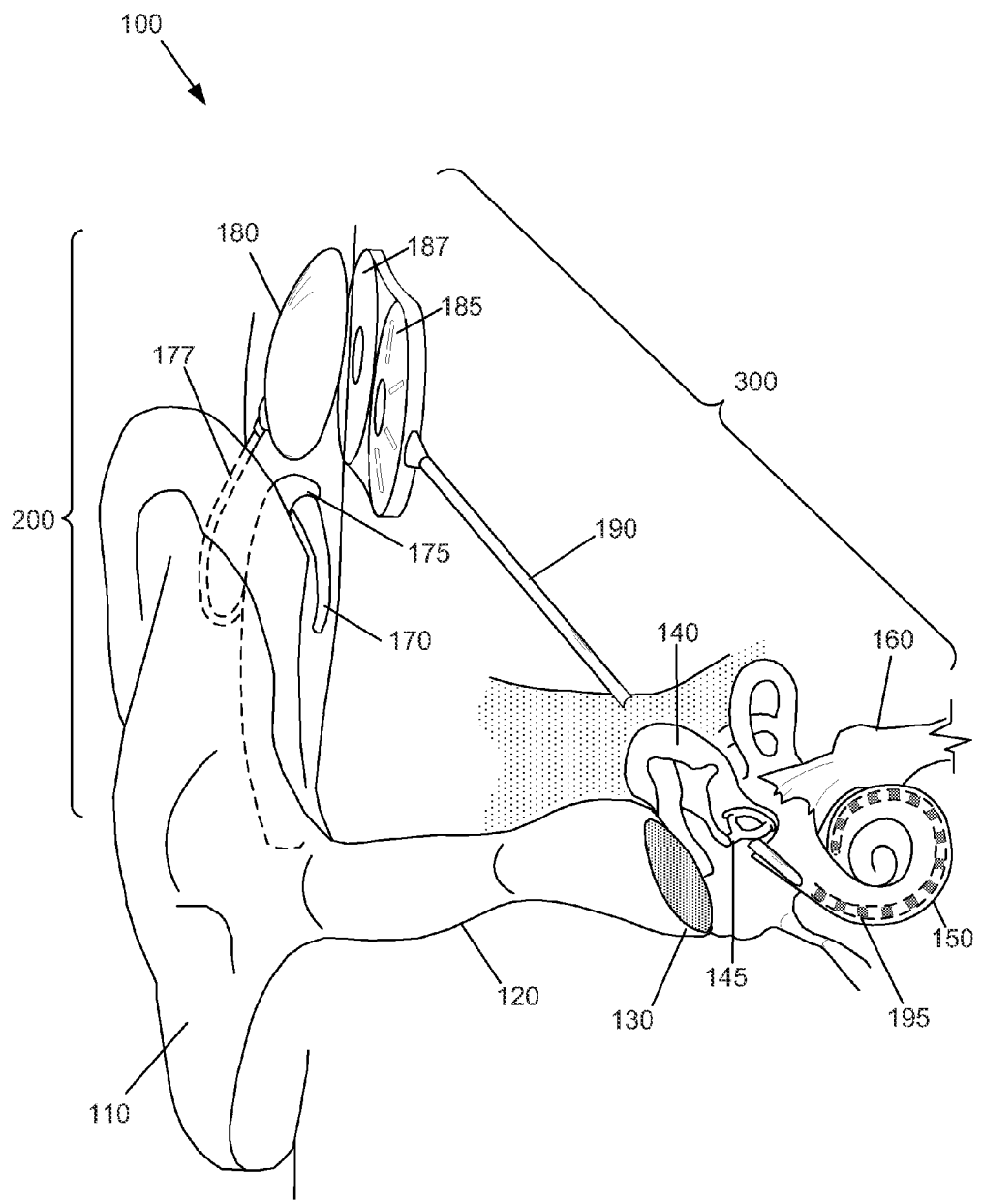
FIG. 1 is a diagram showing an illustrative cochlear implant system in use, according to one example of principles described herein.

In human hearing, hair cells in the cochlea respond to sound waves and produce corresponding auditory nerve impulses. These nerve impulses are then conducted to the brain and perceived as sound.

Hearing loss, which may be due to many different causes, is generally of two types: conductive and sensorineural. Conductive hearing loss typically occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also treatable by surgical procedures.

Many people who are profoundly deaf, however, have sensorineural hearing loss. This type of hearing loss can arise from the absence or the destruction of the hair cells in the cochlea which then no longer transduce acoustic signals into auditory nerve impulses. Individuals with sensorineural hearing loss may be unable to derive significant benefit from conventional hearing aid systems alone, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural deafness, cochlear implant systems, or cochlear prostheses, have been developed that can bypass the hair cells located in the cochlea by presenting electrical stimulation directly to the auditory nerve fibers. This leads to the perception of sound in the brain and provides at least partial restoration of hearing function. Most of these cochlear prosthesis systems treat sensorineural deficit by stimulating the ganglion cells in the cochlea directly using an implanted lead that has an electrode array. Thus, a cochlear prosthesis operates by directly stimulating the auditory nerve cells, bypassing the defective cochlear hair cells that normally transduce acoustic energy into electrical activity to the connected auditory nerve cells.

A cochlear implant system typically comprises both an external unit that receives and processes ambient sound waves and an implanted processor/cochlear lead that receives data from the external unit and uses that data to directly stimulate the auditory nerve. The cochlear lead includes an electrode array that is implanted within one of the cochlear ducts, such as the scala tympani. To minimize damage to sensitive tissues within the patient's cochlea, it can be desirable for the electrode array to be accurately placed within the cochlea using a minimum amount of insertion force. The cochlear implant should be designed so that the insertion forces do not kink or otherwise damage the delicate wires and electrodes contained within the implant.

According to one illustrative embodiment, the electrode array can be constructed from biocompatible silicone, platinum-iridium wires, and platinum electrodes. The portion of the lead to be inserted into the cochlea is designed to be relatively flexible so that it can curve around the helical interior of the cochlea.

This specification describes a stiffening element that provides a desired level of rigidity to the electrode array for improved control by the surgeon and prevents kinking along the length of the cochlear lead during insertion. In some embodiments, the stiffening element extends past the most distal electrode to the tip of the electrode array. This stiffening element can be particularly suited for revision surgeries. The stiffening element is more rigid than the body of the cochlear lead and can be fully encapsulated within the lead to reduce the risk of infection and better stabilize it within the lead. According to one illustrative embodiment, this stiffening element serves at least four purposes. First, the stiffening element provides additional rigidity along the length of the cochlear lead, thereby reducing the likelihood that the insertion forces will kink the lead. Second, the stiffening element provides the surgeon with greater control over the placement of the lead within the cochlea. Third, the stiffening element redirects the insertion force into a tangential force, which allows the cochlear lead to be inserted deeper into the cochlea with less applied force. Fourth, at least a portion of the stiffening element may be formed from a material that plastically deforms during insertion, which allows the stiffening element to conform to the shape of the cochlea and provides the ability to overcome obstructive tissue and provide full insertion of the electrode array.

Revision surgery can be used to explant a cochlear electrode array from the cochlea and replace it with a new electrode array. During revision surgery it is sometimes difficult to insert a compliant pre-curved or lateral electrode array due to the presence of scar tissue/ossification that has formed around the previous electrode array. For a partially ossified cochlea or for a cochlea with fibrous tissue growth, a stiffer electrode can be used to ensure insertion to the full depth of the electrode. In one example, a cochlear lead includes an integral stiffener with suitable malleability. The integral stiffener extends along the complete length of the electrode array and conforms to the shape of the cochlea.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example," or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

FIG. 1 is a diagram showing one illustrative embodiment of a cochlear implant system (100) having a cochlear implant (300) with an electrode array (195) that is surgically placed within the patient's cochlea. Ordinarily, sound enters the external ear, or pinna, (110) and is directed into the auditory canal (120) where the sound wave vibrates the tympanic membrane (130). The motion of the tympanic membrane is amplified and transmitted through the ossicular chain (140), which consists of three bones in the middle ear. The third bone of the ossicular chain (140), the stirrup (145), contacts the outer surface of the cochlea (150) and causes movement of the fluid within the cochlea. Cochlear hair cells respond to the fluid-borne vibration in the cochlea (150) and trigger neural electrical signals that are conducted from the cochlea to the auditory cortex by the auditory nerve (160).

As indicated above, the cochlear implant (300) is a surgically implanted electronic device that provides a sense of sound to a person who is profoundly deaf or severely hard of hearing. In many cases, deafness is caused by the absence or destruction of the hair cells in the cochlea, i.e., sensorineural hearing loss. In the absence of properly functioning hair cells, there is no way auditory nerve impulses can be directly generated from ambient sound. Thus, conventional hearing aids, which amplify external sound waves, provide no benefit to persons suffering from complete sensorineural hearing loss.

Unlike hearing aids, the cochlear implant (300) does not amplify sound, but works by directly stimulating any functioning auditory nerve cells inside the cochlea (150) with electrical impulses representing the ambient acoustic sound. Cochlear prosthesis typically involves the implantation of electrodes into the cochlea. The cochlear implant operates by direct electrical stimulation of the auditory nerve cells, bypassing the defective cochlear hair cells that normally transduce acoustic energy into electrical energy.

External components (200) of the cochlear implant system can include a Behind-The-Ear (BTE) unit (175), which contains the sound processor and has a microphone (170), a cable (177), and a transmitter (180). The microphone (170) picks up sound from the environment and converts it into electrical impulses. The sound processor within the BTE unit (175) selectively filters and manipulates the electrical impulses and sends the processed electrical signals through the cable (177) to the transmitter (180). The transmitter (180) receives the processed electrical signals from the processor and transmits them to the implanted antenna (187) by electromagnetic transmission. In some cochlear implant systems, the transmitter (180) is held in place by magnetic interaction with a magnet (189) in the underlying antenna (187).

The components of the cochlear implant (300) include an internal processor (185), an antenna (187), and a cochlear lead (190) having an electrode array (195). The internal processor (185) and antenna (187) are secured beneath the user's skin, typically above and behind the pinna (110). The antenna (187) receives signals and power from the transmitter (180). The internal processor (185) receives these signals and performs one or more operations on the signals to generate modified signals. These modified signals are then sent through the cochlear lead (190) to the electrode array (195), which is the portion of the cochlear lead (190) that is implanted within the cochlea (150) and provides electrical stimulation to the auditory nerve (160).

The cochlear implant (300) stimulates different portions of the cochlea (150) according to the frequencies detected by the microphone (170), just as a normal functioning ear would experience stimulation at different portions of the cochlea depending on the frequency of sound vibrating the liquid within the cochlea (150). This allows the brain to interpret the frequency of the sound as if the hair cells of the basilar membrane were functioning properly.

The cochlear lead typically comprises an electrode array that is implanted in the scala tympani. The electrode array typically includes several separately connected stimulating electrode contacts, conventionally numbering about 6 to 30, longitudinally disposed on a thin, elongated, flexible carrier. The electrode array is pushed into the scala tympani duct in the cochlea, typically to a depth of about 13 to 30 mm via a cochleostomy or via a surgical opening made in the round window at the basal end of the duct.

In use, the cochlear electrode array delivers electrical current into the fluids and tissues immediately surrounding the individual electrode contacts to create transient potential gradients that, if sufficiently strong, cause the nearby auditory nerve fibers to generate action potentials. The auditory nerve fibers branch from cell bodies located in the spiral ganglion, which lies in the modiolus, adjacent to the inside wall of the scala tympani. The density of electrical current flowing through volume conductors such as tissues and fluids tends to be highest near the electrode contact that is the source of such current. Consequently, stimulation at one contact site tends to selectively activate those spiral ganglion cells and their auditory nerve fibers that are closest to that contact site.

Figure 2:
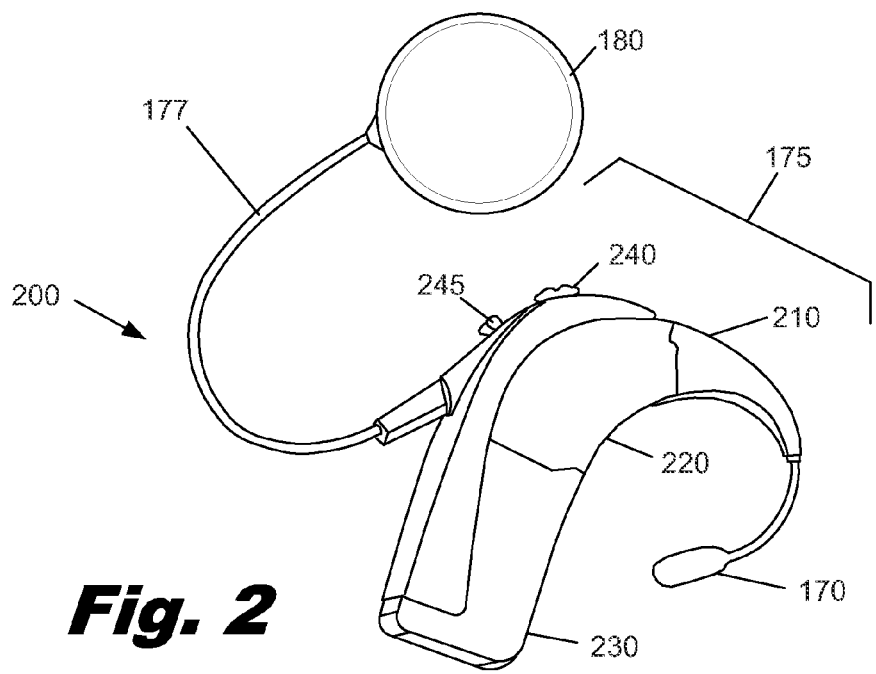
FIG. 2 is a diagram showing external components of an illustrative cochlear implant system, according to one example of principles described herein.

FIG. 2 is an illustrative diagram showing a more detailed view of the external components (200) of one embodiment of a cochlear implant system. External components (200) of the cochlear implant system include a BTE unit (175), which comprises a microphone (170), an ear hook (210), a sound processor (220), and a battery (230), which may be rechargeable. The microphone (170) picks up sound from the environment and converts it into electrical impulses. The sound processor (220) selectively filters and manipulates the electrical impulses and sends the processed electrical signals through a cable (177) to the transmitter (180). A number of controls (240, 245) adjust the operation of the processor (220). These controls may include a volume switch (240) and program selection switch (245). The transmitter (180) receives the processed electrical signals from the processor (220) and transmits these electrical signals and power from the battery (230) to the cochlear implant by electromagnetic transmission.

Figure 3:
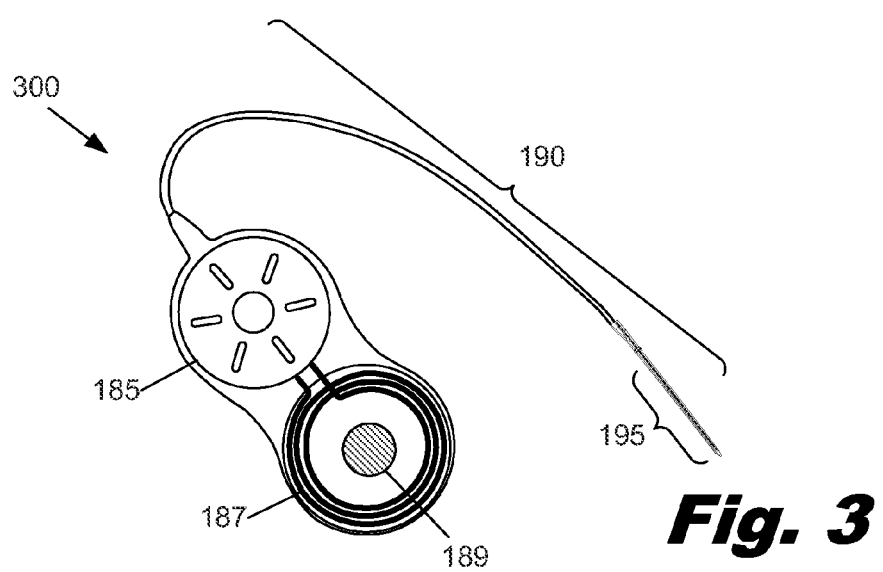
FIG. 3 is a diagram showing the internal components of an illustrative cochlear implant system, according to one example of principles described herein.

FIG. 3 is an illustrative diagram showing one embodiment of a cochlear implant (300), including an internal processor (185), an antenna (187), and a cochlear lead (190) having an electrode array (195). The cochlear implant (300) is surgically implanted such that the electrode array (195) is internal to the cochlea, as shown in FIG. 1. The internal processor (185) and antenna (187) are secured beneath the user's skin, typically above and behind the pinna (110), with the cochlear lead (190) connecting the internal processor (185) to the electrode array (195) within the cochlea. According to one illustrative embodiment, the electrode array (195) is straight or slightly curved before being inserted into the cochlea (150). As discussed below, this particular electrode array (195) is designed for revision surgery. However, the principles described can be applied to a broad range of medical devices. As discussed above, the antenna (187) receives signals from the transmitter (180) and sends the signals to the internal processor (185). The internal processor (185) modifies the signals and passes them through the cochlear lead (190) to the electrode array (195). The electrode array (195) is inserted into the cochlea and provides electrical stimulation to the auditory nerve. This provides the user with sensory input that is a representation of external sound waves sensed by the microphone (170).

Figure 4:
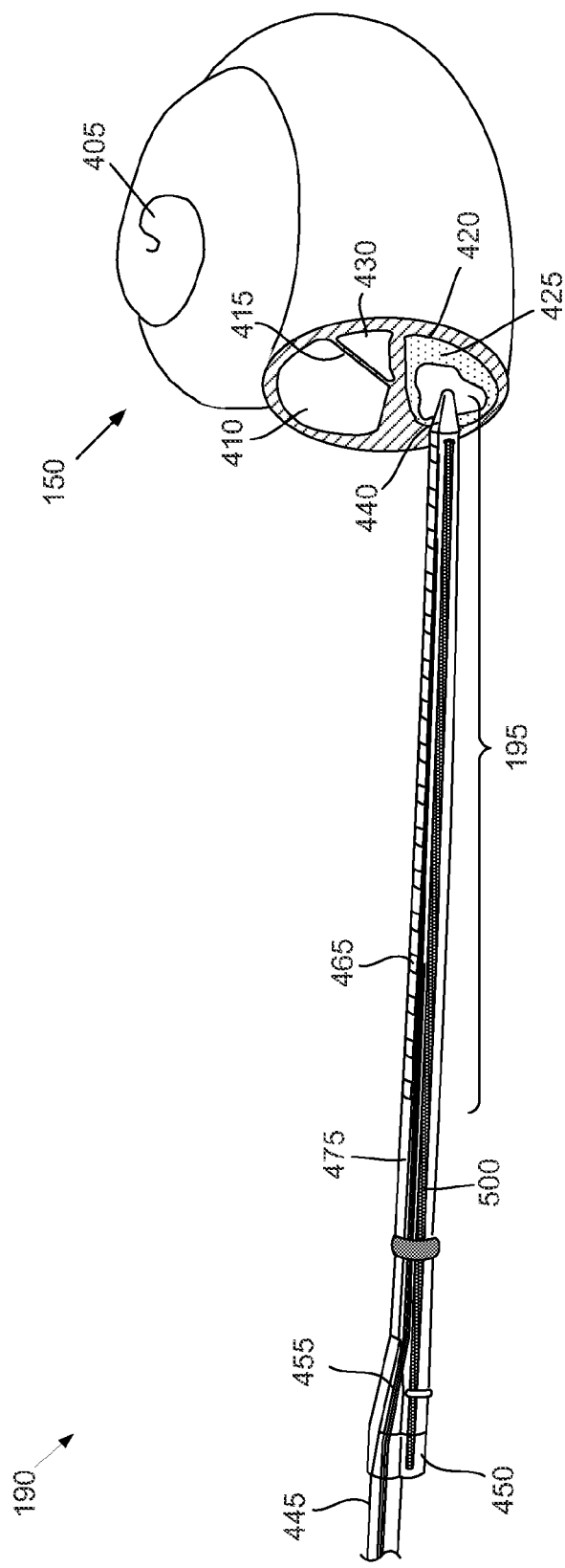
FIG. 4 is a cross-sectional view of a cochlea with an illustrative cochlear lead which includes an electrode array and stiffening element, according to one example of principles described herein.

FIG. 4 is a partially cutaway perspective view of a cochlea (150) and shows an illustrative electrode array (195) being inserted into the cochlea (150). The primary structure of the cochlea is a hollow, helically coiled, tubular bone, similar to a nautilus shell. The coiled tube is divided through most of its length into three fluid-filled spaces (scalae). The scala vestibuli (410) is partitioned from the scala media (430) by Reissner's membrane (415) and lies superior to it. The scala tympani (420) is partitioned from the scala media (430) by the basilar membrane (425) and lies inferior to it. A typical human cochlea includes approximately two and a half helical turns of its constituent channels. The cochlear lead (190) is inserted into one of the scalae, typically the scala tympani (420), to bring the individual electrodes into close proximity with the tonotopically organized nerves.

Throughout the specification and appended claims the term "distal" refers to portions that are closer to the tip (440) of the cochlear lead (190) and "proximal" refers to portions that are farther away from the tip (440). The terms "medial" and "lateral" refer to locations that are closer to the center of the cochlea and closer to the outer portions of the cochlea, respectively. For example, the phrase medial wall of the cochlea refers to portions of a cochlear duct that are toward the center of the cochlea.

In the example shown in FIG. 4, the scala tympani (420) is narrowed by ossification (425). The ossification and other obstructions in the scala may form for a variety of reasons, including foreign body reaction to a previous electrode array. The ossification or other obstructions may partially block the scala and make the insertion of a new electrode array during revision surgery challenging. In particular, the surgeon may need increased control to maneuver the electrode array around or through the obstructions. Higher forces may be needed to successfully insert the electrode array to the desired insertion depth. The combination of higher forces and obstructions can lead to kinking or folding of the electrode array. In one embodiment, it can be desirable to insert the electrode array to 360 degrees or approximately the same depth as the previous electrode array.

The illustrative cochlear lead (190) is specifically designed to provide the surgeon with the desired control and prevent the electrode array from kinking or folding along its length. The cochlear lead (190) includes a lead body (445). The lead body (445) connects the electrode array (195) to the internal processor (185, FIG. 3). A number of wires (455) pass through the lead body (445) to bring electrical signals from the internal processor (185, FIG. 3) to the electrode array (195). According to one illustrative embodiment, proximal of the electrode array (195) is a molded silicone rubber feature (450). The feature (450) can serve a variety of functions, including, but not limited to, providing a structure that can be gripped or pushed by an insertion tool and providing a visual indicator of how far the cochlear lead (190) has been inserted.

The wires (455) that conduct the electrical signals generated by the processor are connected to the electrodes (465) within the electrode array (195). For example, electrical signals which correspond to a low frequency sound may be communicated via a first wire to an electrode near the tip (440) of the electrode array (195). Electrical signals which correspond to a high frequency sound may be communicated by a second wire to an electrode (465) near the proximal end of the electrode array (195). According to one illustrative embodiment, there may be one wire (455) for each electrode (465) within the electrode array (195). The internal processor (185, FIG. 3) may then control the electrical field generated by each electrode individually. For example, one electrode may be designated as a ground electrode. The remainder of the electrodes may then generate electrical fields which correspond to various frequencies of sound. Additionally or alternatively, adjacent electrodes may be paired, with one electrode serving as a ground and the other electrode being actively driven to produce the desired electrical field.

According to one illustrative embodiment, the wires (455) and portions of the electrodes (465) are encased in a flexible body (475). The flexible body (475) may be formed from a variety of biocompatible materials, including, but not limited to, medical grade silicone rubber. The flexible body (475) secures and protects the wires (455) and electrodes (465). The flexible body (475) allows the electrode array (195) to bend and conform to the geometry of the cochlea. When placed within the cochlea (150), the electrode array (195) brings the individual electrodes into close proximity with the tonotopically organized nerves in the cochlea (150).

Additionally, as can be seen in FIG. 4, and described further below, a stiffening element (500) extends from the molded silicone rubber feature (450) to the tip (440) of the electrode array (195). The stiffening element (500) allows the cochlear lead to be more precisely positioned within the cochlea and reduces the propensity of the cochlear lead (190) to kink. In embodiments where the stiffening element (500) is plastically deformable, the stiffening element (500) conforms to the curvature of the cochlea during insertion. This can help prevent undesirable motion of the lead within the cochlea. The stiffening element and its function are described in more detail below.

FIGS. 5A and 5B are detail views of an illustrative stiffening element. FIG. 5A is a side view of an illustrative stiffener (515) and sheath (540). The sheath (540) is placed over the stiffener (515) to form the stiffening element. According to one illustrative embodiment, the sheath (540) may be formed from PTFE or other polymer. For example, the sheath (540) may be formed from expanded PTFE. Expanded PTFE has high strength, chemical inertness, and a much lower modulus of elasticity than unexpanded PTFE. According to one illustrative embodiment, the expanded PTFE sheath or liner may be a tube with an inside diameter of 0.006 inches and an outside diameter of 0.007 inches. Additionally, the size and shape of the sheath (540) may be selected to allow more or less relative motion between the stiffening element (500) and the sheath and between the sheath and the flexible body (475). For example, in some embodiments, the sheath (540) may be sized to fit relatively loosely over the stiffening element (500). This will allow the stiffening element (500) to slide within the sheath (540) relatively easily. Alternatively, the sheath (540) may be sized to fit more tightly around the stiffening element (500). In this embodiment, there may be little or no relative motion of the stiffening element (500) within the sheath (540). Instead, the relative motion of the stiffening element (500) with respect to the flexible body (475, FIG. 5) may take place primarily at the interface between the outer surface of the sheath (540) and the inner surface of the flexible body.

In some embodiments, the fit of the sheath (540) over the stiffening element may vary from location to location. For example, the sheath (540) may be formed so that it fits relatively loosely over the stiffening element (500) near its proximal and distal ends, but have a tighter fit in the center of the stiffening element. Additionally, the sheath (540) may cover the entire stiffening element (500) or only a portion of the stiffening element (500). For example, the sheath (540) may cover only the distal portion (515) of the stiffening element. Although the sheath (540) is shown with an open end and a closed end, the sheath may have both ends open or both ends closed.

FIG. 5B shows a cross-section of an illustrative stiffening element (500) with the sheath (540) in place over the stiffener (515). A cap (545) has been place over the distal end of the stiffening element. The cap (545) may be formed from the same or different material than the sheath (540). The cap (545) may be bonded to the tip of the stiffening element (500) or may be an integral part of the sheath (540).

Figure 5C:
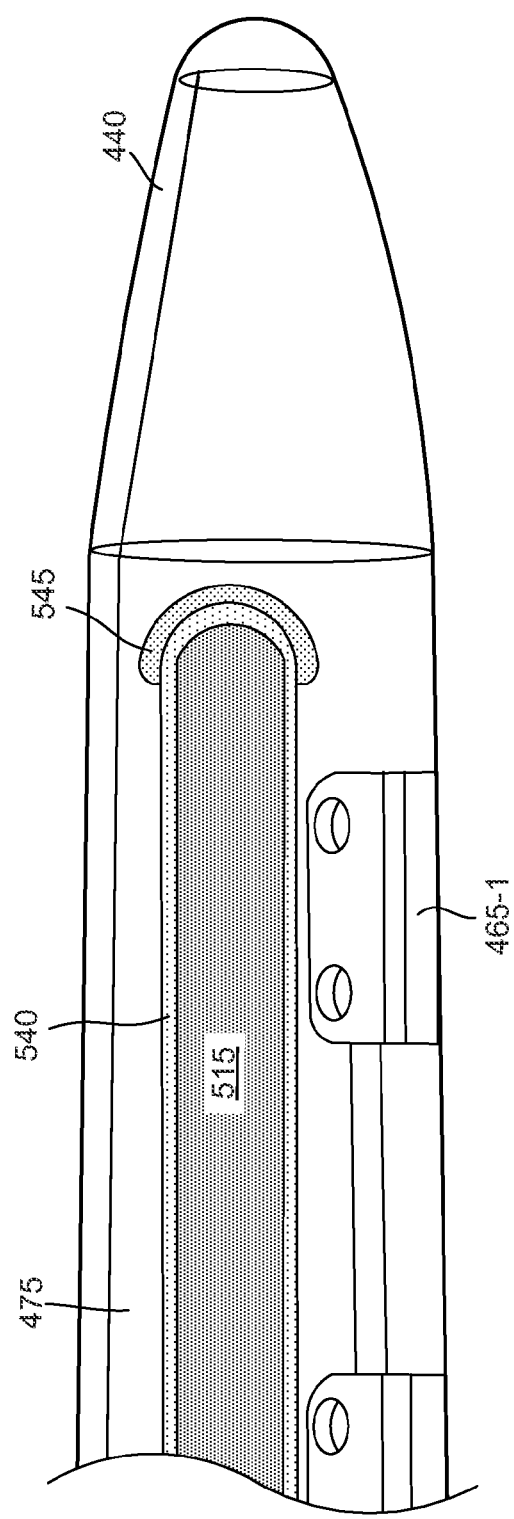
FIG. 5C shows a cross-section of a tip of an illustrative cochlear lead, according to one example of principles described herein.

FIG. 5C shows a cross-section of a distal portion of an illustrative cochlear lead. As shown in the figure, the stiffening element extends past the most distal electrode (465-1), with the cap (540) being located between the most distal electrode (465-1) and the tip (440) of the electrode array. The cap (545) may serve a number of purposes, including distributing the insertion forces over a larger area and preventing the stiffening element (500) from penetrating the flexible body (475).

FIG. 6A is a partial side view of an illustrative cochlear lead (190). As discussed above, the cochlear lead (190) includes an electrode array (195) comprising electrodes (465), a lead body (445) carrying wires (455) that extend from the internal processor (185, FIG. 3) to the electrodes (465), a flexible body (475) on which electrodes (465) are disposed, a stiffening element (500) disposed within a portion of the flexible body (475), and a molded silicone rubber feature (450) proximal of the electrode array (195). The illustrative cochlear lead (190) further includes a cochleostomy marker (466) as a guide for positioning the electrode array (195). When the electrode array (195) is properly positioned within the cochlea, the cochleostomy marker (466) is positioned at or near the cochleostomy, and, the electrodes (465) are well positioned to stimulate the tonotopically-arranged groups of nerve endings.

The stiffening element (500) may be located within the flexible body (475) and extend from at or near the molded feature (450) to a location within the electrode array (195). According to one embodiment, the stiffening element (500) comprises or consists essentially of platinum. In other embodiments, it may be made of any material which provides the desired mechanical and chemical properties. These properties may include low yield strength and chemical inertness. By way of example and not limitation, the stiffening element (500) may be a plastic, metal, glass, composite, or other material. According to one illustrative embodiment, the stiffening element (500) may comprise or consist of gold or a gold alloy.

According to one embodiment, stiffening element (500) extends approximately 2 mm to 6 mm from the cochleostomy. For example, the stiffening element may extend into the cochlea approximately 15 mm to 30 mm from the cochleostomy. In this illustrative embodiment, the stiffening element (500) extends from the molded rubber gripping feature (450) through the electrode array past the most distal electrode. The gripping feature (450) can be grasped by general or specialized surgical tools. The extension of the stiffening element into the gripping feature (450) allows these tools to grip the stiffening element through the encapsulation with minimal risk of damage to other components in the cochlear lead. The stiffening element can then be manipulated using the surgical tools to guide the cochlear lead into the desired position within the cochlea.

FIG. 6B shows a cross-section along line 6B-6B of a portion of the illustrative cochlear lead (190) in which the stiffening element (500) is disposed. The wires (455) may be shaped into a wire bundle by the electrode (465). Portions of the electrode, the wires, and the stiffening element (500) are encapsulated by the flexible body (475). In this particular embodiment, the electrodes (465) are disposed within the flexible body (475) on the medial wall of the electrode array. The stiffening element (500) is disposed in flexible body (475) opposite the electrodes (465).

FIG. 6C is a cross-sectional diagram along line 6C-6C taken through the distal end of the stiffening element (500). Because the distal end of the stiffening element (500) extends beyond the most distal electrode (465-1), only the cross section of the stiffening element (500) is shown within the flexible body (475). The cross sectional view shows the stiffener (515) surrounded by the sheath (540) and the cap (545).

The stiffness and ductility of the stiffening element (500) can be selected to significantly influence the amount of force required to insert the electrode array (195) into the cochlea.

Alternatively or additionally, the geometry of the stiffening element can be altered along its length to create the desired mechanical properties. For example, the distal portion of the stiffener may have a variety of cross sectional geometries, including flattened, elliptical or circular. The cross sections may vary along the length of the stiffener. These cross sections can be selected to produce the desired stiffness, with lower stiffnesses typically desired near the distal end of the stiffener. The different cross sections may be formed in a variety of ways, including grinding, rolling, pressing, drawing, or other suitable technique. In some embodiments, the distal portion of the stiffener may have a number of micromachined features that produce desired bending characteristics.

Figures 7A, 7B, 7C:
FIGS. 7A-7C are cross sectional diagrams of steps in an illustrative process for making a cochlear lead with an integral stiffening element, according to one example of principles described herein.

FIGS. 7A-7C are cross sectional diagrams of steps in an illustrative process for making a cochlear lead with an integral stiffening element. In a first step, a stiffener (700) is shaped and annealed. The shaping process may include cutting the stiffener (700) to the desired length. In embodiments where the stiffening element is a metal, the distal portion (515) may be annealed. Annealing is a versatile heat treating process which alters the material properties (such as yield strength and ductility) of a metal. According to one illustrative example, the stiffener (700) may include platinum or a platinum alloy. In some embodiments, the stiffener (700) may consist essentially of platinum. Annealing may be used to produce a distal portion (710) having greater ductility and lower stiffness than the rest of the stiffener (700). This allows the distal portion to bend more easily to follow the curvature of the cochlear ducts. Further, annealing will allow the distal portion to maintain its bent shape after insertion into the cochlea. This can assist in holding the electrode array in place within the cochlea. For example, a distal portion (515) with high yield strength of 185 to 205 MPa may be more susceptible to migrate out from the cochlea due to strain energy. Conversely, a distal portion with a lower yield strength of 14 to 35 MPa may plastically conform to the shape of the cochlea and have a tendency to retain the electrode array in the cochlea.

A variety of other techniques, such as work hardening, could be used to modify the yield strength, malleability, ductility, stiffness, or other characteristics of the stiffener (700). According to one example, the distal portion (710) of the stiffener (700) is annealed and the tip portion (705) is annealed so that the metal is "dead soft." The term "dead soft" refers to the condition of maximum softness that is attainable in a metal or metal alloy through annealing. In other embodiments, the distal portion may be annealed but not to the extent that the metal is dead soft.

The annealing may be performed in a stepwise fashion, the entire tip portion (705) having a substantially uniform dead soft anneal and the remainder of the distal portion (710) being annealed to a lesser extent. The temper of the remainder of the stiffener (700) may remain in an "as drawn" state or may be heat treated to alter characteristics of the metal. In one embodiment, portions of the electrode that will be bent to follow the spiral of the cochlea are annealed and portions that remain in the relatively straight basal portion of the cochlea are more rigid. In alternative embodiments, the annealing may vary continuously along the length of the stiffener (700). According to one embodiment, the stiffener may be annealed from the distal tip up to approximately its midpoint.

The sheath (715) is formed by cutting it to length. In this example, the distal end (725) is closed while the proximal end (720) of the sheath is open. The sheath (715) is cut slightly longer than the stiffener. As discussed above, the sheath (715) may be sized to allow for motion of the stiffener (700) within it.

FIG. 7B shows the stiffener (700) inserted into the sheath (715). The proximal end (720) of the sheath is then fused or adhered shut. The stiffener is then entirely enclosed in the sheath to form the stiffening element (500). In some embodiments, the sheath may be substantially impermeable.

FIG. 7C is a side view of an illustrative cochlear lead (190) that includes the stiffening element (500), with the proximal end of the stiffening element (500) extending into the molded silicone rubber feature (450) and its distal end (725) extending to the tip (440) of the cochlear lead (190).

The sheath is only one illustrative example. In other examples, the stiffener (515) may be overcoated with a thin layer. This thin layer may be formed from a number of materials and applied in a variety of ways. In other embodiments, the flexible body may include a lumen may be lined with polytetrafluoroethylene (PTFE) or other friction reducing material. The stiffener can then be inserted into the lumen. In most cases, the stiffener can move relative to the flexible body (475, FIG. 4) during bending. This reduces the overall bending stiffness of the cochlear lead (190) while still maintaining its resistance to kinking.

Figure 8:
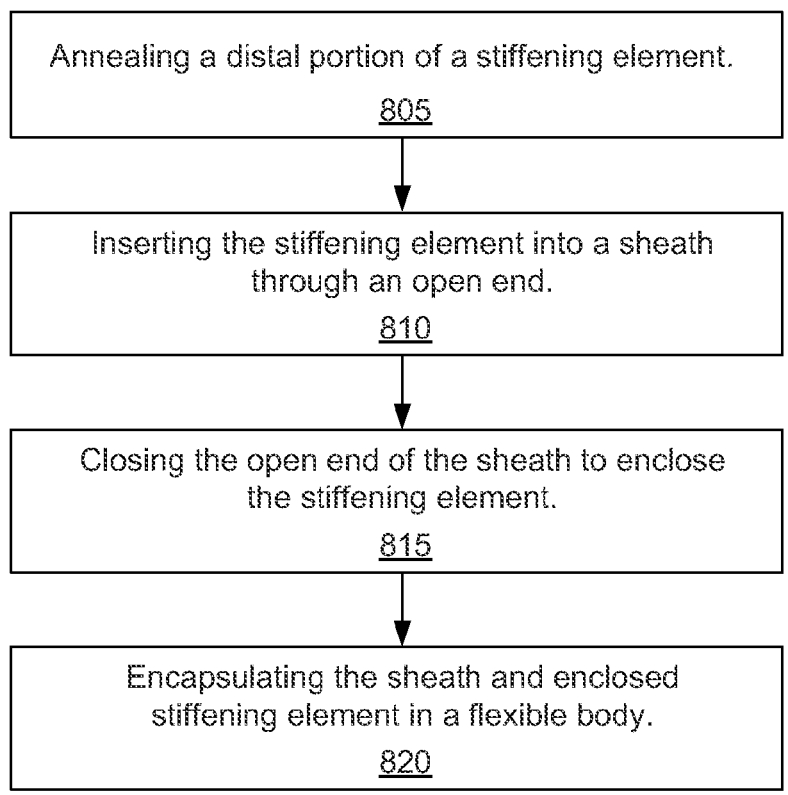
FIG. 8 is a flowchart showing an illustrative method for forming a cochlear lead, according to one example of principles described herein.

FIG. 8 is a flowchart showing an illustrative method for forming a cochlear lead. A stiffener is formed with the desired material, diameter, and length. For example, the stiffener may comprise or substantially consist of platinum. The distal portion of the stiffener is then annealed (step 805) so that the distal portion of the stiffener is substantially softer than a proximal portion. In some embodiments, the distal portion is approximately half of the total length the stiffener. In some implementations a tip portion of the stiffener may be annealed so that it is dead soft. The tip portion may be one quarter or less of the total length of the stiffener.

The sheath is then formed. As discussed above, the sheath may be a polymer tube that is selected to allow the stiffener to slide freely within its inner diameter. Additionally, the polymer material may be selected for its lubricity and biocompatibility. One end of the tube is closed, with the other end remaining open to receive the stiffener.

In some embodiments an additional cap is placed over the distal end of the sheath. The cap may be a flat plate or semi spherical shape that prevents puncture of the stiffening element through the flexible body. The cap may be used alone or in conjunction with the sheath. In other embodiment, the sheath is fused together to form a ball or caplike structure.

The stiffener is inserted into the sheath (step 810) and the ends of the sheath are closed (step 815). The sheath and the stiffener make up the stiffening element. The stiffening element is then encapsulated in the flexible body (step 820) with the electrodes and wires. A variety of techniques can be used to encapsulate the stiffening element in the flexible body. Illustrative examples of these techniques are described in U.S. application Ser. No. 12/789,264, filed May 27, 2010, entitled "Cochlear Lead" to Chuladatta Thenuwara et al., which was incorporated by reference above.

A variety of other steps can be taken to complete the manufacture of the cochlear lead. For example, these steps may include testing, sterilization, and packaging.

FIG. 9 is a flowchart showing an illustrative method for surgically implanting using a cochlear lead with a full length stiffening element during a revision surgery. The patient is prepared and the appropriate surgical openings made. The existing cochlear implant is removed from the patient, including removing a previous cochlear lead from the cochlea (step 905). The new cochlear implant, including a replacement cochlear lead with a full length slidably encapsulated stiffening element, is taken from its packaging (step 910). The replacement cochlear lead includes an offset gripping feature. The stiffening element extends from within the offset gripping feature through the electrode array and past the most distal electrode. In some instances, the new cochlear electrode array may have a smaller diameter than the cochlear electrode which was removed from the patient. This may allow for the new cochlear electrode to be more easily inserted into the opening that previously contained the old cochlear electrode.

The surgeon attaches the appropriate tool to the cochlear lead by gripping a proximal end of the stiffening element contained within the gripping feature (step 915). This tool may be a special purpose tool that is specifically adapted for insertion of the cochlear lead or may be a more general purpose surgical tool such as tweezers or forceps. In some cases, the surgeon may manually bend the distal portion of the cochlear lead to achieve the desired curvature. Because the distal portion of the cochlear lead is annealed, the cochlear lead will tend to maintain the curvature created by the surgeon. In other examples, the surgeon may leave the cochlear lead in its substantially straight configuration.

The surgeon then inserts the electrode array into the patient's cochlea by manipulating the proximal end of the stiffening element to guide the cochlear lead into the cavity vacated by the previous cochlear lead (step 920). The full length stiffening element provides the surgeon with increased control throughout the insertion process and allows slightly higher forces to be used without kinking or folding over the electrode array. The surgeon can use the increased control and resistance to kinking provided by the stiffening element to maneuver the cochlear lead past obstructions to a predetermined depth in the cochlea.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A cochlear lead comprising:
   a plurality of electrodes configured to stimulate an auditory nerve from within a cochlea;
   a flexible body supporting the plurality of electrodes along a length of the flexible body; and
   a stiffening element slidably encapsulated within the flexible body, the stiffening element extending past a most distal electrode, wherein a distal portion of the stiffening element plastically deforms upon insertion into a curved portion of the cochlea.

2. The cochlear lead of claim 1, wherein the stiffening element comprises a barrier element at least partially surrounding the stiffening element, and wherein at least portions of the stiffening element translate with respect to the flexible body when the cochlear lead bends.

3. The cochlear lead of claim 2, wherein the barrier element comprises a sheath that forms a physical barrier between exterior fluids and the stiffening element.

4. The cochlear lead of claim 3, wherein the sheath is a polymer coating adhered to the stiffening element, wherein the polymer coating and stiffening element slide with respect to the flexible body when the cochlear lead bends.

5. The cochlear lead of claim 3, wherein the sheath is closed on both ends and entirely surrounds the stiffening element.

6. The cochlear lead of claim 3, wherein the sheath is a polymer sock having an inner diameter sized such that the stiffening element slides within the polymer sock.

7. The cochlear lead of claim 1, further comprising a gripping feature extending from one side of the flexible body, wherein the stiffening element extends into the gripping feature.

8. The cochlear lead of claim 1, further comprising a cap on a distal end of the stiffening element.

9. The cochlear lead of claim 8, wherein the cap is disposed over a sheath surrounding the stiffening element.

10. The cochlear lead of claim 1, wherein the cochlear lead is substantially straight and has a radius of curvature of no more than 20 mm when the cochlear lead is in its relaxed state.

11. The cochlear lead of claim 1 wherein the distal portion of the stiffening element is dead soft.

12. The cochlear lead of claim 11, wherein the stiffening element consists essentially of platinum.

13. The cochlear lead of claim 11, wherein the stiffening element is annealed to approximately a midpoint of the stiffening element.

14. A cochlear lead comprising:
    a plurality of electrodes configured to stimulate an auditory nerve from within a cochlea;
    a flexible body supporting the plurality of electrodes along a length of the flexible body; and
    a stiffening element slidably encapsulated within the flexible body, the cochlear lead being substantially straight and having a radius of curvature of no more than 20 mm when the cochlear lead is in its relaxed state,
    wherein the stiffening element is annealed to approximately its midpoint with a distal portion of the stiffening element being dead soft and the cochlear lead positioned such that a portion of the stiffening element plastically deforms upon insertion into a curved portion of the cochlea and at least portions of the stiffening element translate with respect to the flexible body when the cochlear lead bends;
    a sheath between the flexible body and the stiffening element, wherein the sheath is closed on both ends and surrounds the stiffening element; and
    a gripping feature extending from one side of the flexible body, wherein the stiffening element extends from the gripping feature through the flexible body past the most distal electrode.

15. A method for forming a cochlear lead comprising:
    annealing a distal portion of a stiffening element;
    inserting the stiffening element into a sheath through an open end;
    closing the open end of the sheath to enclose the stiffening element; and
    encapsulating the sheath and enclosed stiffening element in a flexible body, wherein the flexible body comprises an array of electrodes disposed along a length of the flexible body, wherein the stiffening element extends past a most distal electrode of said array.

16. The method of claim 15, further comprising placing a cap on a distal end of the stiffening element.

17. The method of claim 15, wherein the sheath comprises polytetrafluoroethylene.

18. The method of claim 15, wherein closing the open end of the sheath comprises heating and compressing the open end of the sheath.

* * * * *